United States Patent [19]

Johnson

[11] Patent Number: 5,214,190

[45] Date of Patent: May 25, 1993

[54] NITROPHENYL ETHER HERBICIDES

[76] Inventor: Wayne O. Johnson, 346 Centennial Rd., Warminster, Pa. 18974

[21] Appl. No.: 964,577

[22] Filed: Oct. 21, 1992

Related U.S. Application Data

[60] Continuation of Ser. No. 559,653, Jan. 23, 1984, abandoned, which is a division of Ser. No. 104,598, Dec. 17, 1979, abandoned.

[51] Int. Cl.$^5$ ............................................. C07C 205/00
[52] U.S. Cl. ........................................................ 560/21
[58] Field of Search ........................................... 560/21

[56] References Cited

U.S. PATENT DOCUMENTS 3,717,669  2/1973  Grant et al. ............................ 560/21

Primary Examiner—Paul J. Killos

[57] ABSTRACT

Compounds of the formula:

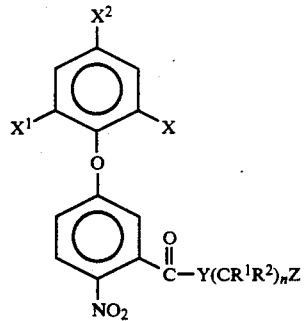

wherein X is hydrogen, halo, trihalomethyl, alkyl, nitro, or cyano; $X^1$ is hydrogen, halo, or trihalomethyl; $X^2$ is trihalomethyl or halo; Y is O, S, NH or $NR^1$; $R^1$ and $R^2$ are the same or different radicals selected from hydrogen, alkyl, or mononuclear aralkyl; n is 1 to 5, and Z is carboxy, amino, mono- and dialkyl amino and when Z is carboxy, the agronomically acceptable salts, esters, thioesters and amides thereof, and compositions containing these compounds exhibit herbicidal activity.

4 Claims, No Drawings

NITROPHENYL ETHER HERBICIDES

This is a continuation of copending application Ser. No. 061,559,653 filed on Jan. 23, 198, now abandoned, which is a continuation of 06/104,598 filed Dec. 17, 1979 now abandoned.

This invention relates to nitrodiphenyl ethers, compositions containing nitrodiphenyl ethers and to methods of controlling weeds.

Diphenyl ethers are known to be effective weed control agents. See for example U.S. Pat. Nos. 3,928,416; 3,454,392; 3,798,276; 3,873,303; 4,001,005; and 4,029,493 among the many patents issued. However, even now herbicidal effectiveness of a diphenyl ether cannot be predicted knowing only the structures and often quite closely related compounds will have quite different weed control abilities. See, *Advances in Agronomy*, Vol. 24, pages 331, 332, 355, 356, 357 and 358, *Herbicides, Chemical Degradation and Mode of Action*, Kearney and Kaufman, Vol. 2, Dekker, Inc. pages 552–563 and 728–737 and *Mode of Action of Herbicides*, Ashton and Crafts and also U.S. Pat. Nos. 3,454,392 and 3,776,961. An ideal herbicide should give selective weed control, over the full growing season, with a single administration at low rates of application. It should be able to control all common weeds by killing them as the seed, the germinating seed, the seedling, and the growing plant. At the same time, the herbicide should be substantially non-phytotoxic to the crops to which it is applied and should decompose or otherwise be dissipated so as not to poison the soil permanently. The known diphenyl ether herbicides fall short of these ideals and thus the search continues to discover new herbicides which are more selective or which complement the known diphenyl ethers.

In accordance with the present invention, there is provided a new class of diphenyl ether herbicides having the following structural formula:

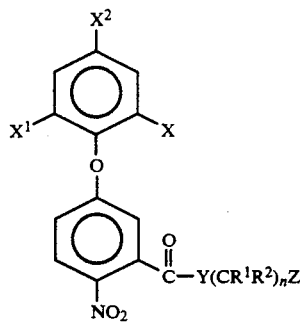

wherein X is hydrogen, halo, for example, bromo, chloro, fluoro, iodo and the like, trihalomethyl, for example, trifluoromethyl and the like, alkyl, for example, lower alkyl of from 1 to 4 carbon atoms, such as methyl, ethyl, and the like, cyano or ntro; $X^1$ is hydrogen, halo, for example, bromo, chloro, fluoro, iodo and the like, or trihalomethyl, such as trifluoromethyl and the like; $X^2$ is trihalomethyl such as trifluoromethyl and the like or halo, such as chloro, bromo, fluoro and the like; Y is O, NH, $NR^1$ or S; $R^1$ and $R^2$ are the same or different radicals selected from hydrogen, lower alkyl of from 1 to 4 carbon atoms, mononuclear aryl lower alkyl, such as benzyl, phenethyl and the like; n is an integer of from 1 to 5 and Z carboxy, amino, mono- and dialkylamino, for example mono- and di lower alkylamino such as methylamino, ethylamino, propylamino, butylamino, dimethylamino, diethylamino, dpropylamino, dibutylamino and the like and when Z is carboxy the agronomically acceptable salts, esters and amides thereof. Examples of salts include the alkali metal and alkaline earth metal salts, such as lithium, sodium, potassium, magnesium and the like. Examples of esters include saturated and unsaturated, substituted and unsubstituted alkyl esters, preferably lower alkyl esters of from 1 to 6 carbon atoms, such as the methyl, ethyl, propyl, butyl, tert- butyl, pentyl and hexyl esters wherein the substituents on the alkyl may be selected from alkoxy, for example, lower alkoxy, such as methoxy, ethoxy, propoxy, butoxy and the like, haloalkoxy, for example, halo lower alkoxy such as chloroethoxy, bromoethoxy and the like, trihalomethylalkoxy for example, trifluoromethyl lower alkoxy such as trifluoromethylmethoxy and the like. Also included are unsaturated esters of from 3 to 5 carbon atoms, for example, allyl, propynyl, α-methylallyl, α-ethylallyl, and the like.

A preferred embodiment of this invention relates to compounds of the formula:

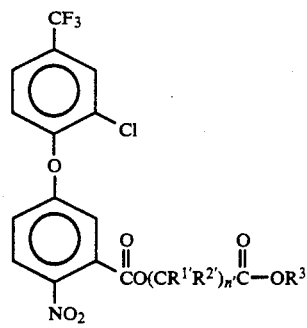

wherein $R^1$ and $R^2$ are selected from hydrogen or lower alkyl; n' is an integer of 1 or 2 and $R^3$ is hydrogen, saturated, unsaturated, substituted or unsubstituted alkyl, for example, saturated, unsaturated, substituted or unsubstituted lower alkyl of from 1 to 6 carbon atoms, such as, methyl, ethyl, n-propyl, iso-propyl, n-butyl, sec-butyl, tert-butyl, n-pentyl, n-hexyl and the like, unsaturated lower alkyl of from 3 to 5 carbon atoms such as allyl and the like, trifluoromethyl lower alkyl for example, trfluoromethylmethyl and the like, an alkali metal cation for example lithium, sodium, potassium and the like or an alkalne earth metal cation, for example, calcium, magnesium and the like. These compounds exhibit particularly good herbicidal activity.

Examples of the compounds of the invention embraced by Formula I include:

2-chloro-4-trifluoromethyl-3'-carbomethoxymethoxycarbonyl-4'-nitrodiphenyl ether, 2,4,6-trichloro-3'-carbomethoxymethoxycarbonyl-4'nitrodiphenyl ether, 2,4-dichloro-3'-carboxymethoxycarbonyl-4'-nitrodiphenyl ether, 2-chloro-4-trifluoromethyl-3'-sodiocarboxymethoxy-(carbonyl-4'-nitrodiphenyl ether, 2-fluoro-4,6-dichloro-3'-N(carbomethoxymethyl)-carbamyl-4'-nitrodiphenyl ether, 2-fluoro-4-trifluoromethyl-3'-(1-carbomethoxy)-propylthiocarbonyl-4'-nitrodiphenyl ether, 2-fluoro-4-trifluoromethyl-6-chloro-3'-(1-allyloxy-carbonyl)butoxycarbonyl-4'-nitrodiphenyl ether 2,4,6-trichloro-3'-carbo(2-methoxy)ethoxymethoxycarbonyl-4'-nitrodiphenyl ether, 2-bromo-4-trifluoromethyl-3'-(2-carbomethoxy)ethoxyo-carbonyl-4'-nitrodiphenyl ether, 2-methyl-4-trifluoromethyl-3'-(1-carbomethoxy)phenethoxycarbonyl-4'-nitrodiphenyl ether, 2-cyano-4-trifluoromethyl-3'-w-carbomethoxypentoxycarbonyl-4'-nitrodiphenyl ether, 2-nitro-4-chloro-3'-carbotrifluoroethoxymethoxycarbonyl-4'-nitrodiphenyl ether, 2-fluoro-4-bromo-3'-carbamylmethoxycarbonyl-4'-nitrodiphenyl ether, 2,4,6-trchloro-3'-(1-N-dimethylcarbamyl)phenethoxycarbonyl-4'-nitrodiphenyl ether, 4-trifluoro-3'-(1-carbomethoxy)benzyloxycarbonyl-4'nitrodiphenyl ether, 2,4-dichloro-3'-(1-carbomethoxyisopropoxycarbonyl)-4'-nitrodiphenyl ether 2,4,6-trichloro-3'-(1-carbomethoxysopropoxycarbonyl)-4'-nitrodiphenyl ether, 2,4-dichloro-3'-(1-carbomethoxyisobutoxycarbonyl)-4'-nitrodiphenyl ether, 2-fluoro-4,6-dichloro-3'-(1-carbomethoxyisopropoxycarbonyl)-4'-nitrodiphenyl ether, 2,4-dichloro-3'-(1-carbomethoxy-2-phenylethoxycarbonyl)-4'-nitrodiphenyl ether, 2,4,6-trichloro-3'-(2-carbomethoxyisopropoxycarbonyl)-4'-nitrodiphenyl ether, 2,4-dichloro-3'-(1-methyl-3-carbomethoxypropoxycarb-onyl)-4'-nitrodiphenyl ether, 2,4,6-trichloro-3'-(3-carbomethoxypropoxycarbonyl)-4'-nitrodiphenyl ether, and 2,4-dichloro-3'-(4-carbomethoxy-n-butoxycarbonyl)-4'nitrodiphenyl ether.

The products of this invention may be prepared by one of four methods which comprises treating an acid halide with an alkoxy substituted compound; by treating an alkali metal or alkaline earth metal carboxylate with a halo substituted compound and where necessary treating the intermediate with a nitrating agent or by treating an alkali metal phenoxide with an appropriately substituted 5-halo-2-nitrobenzene.

The first process comprises treating 4-substituted phenyl-3'-halocarbonyl-4'-nitrophenyl ether (II) with an appropriate compound in the presence of an inert solvent, such as toluene and the like, optionally, in the presence of an acid acceptor. The reaction may be conducted at a temperature in the range of from about 20° to about 150° C. for a period of time of from about 15 minutes to about 24 hours; however, the reaction is generally conducted at 30° to 40° C. for a period of time of about 2 hours. The following equation illustrates this process:

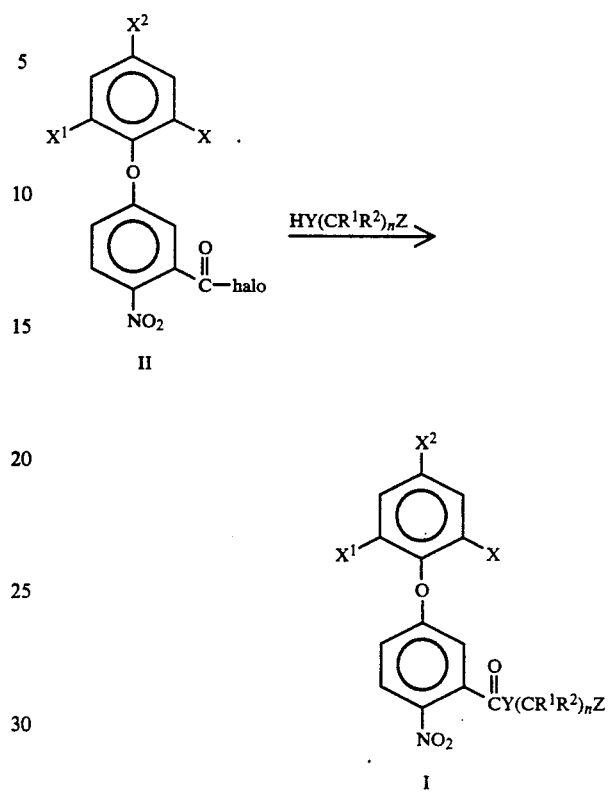

wherein X, $X^1$, $X^2$, Y, $R^1$, $R^2$, n and Z are as defined above and halo is chloro, bromo and the like.

The second process comprises treating 4-substituted phenyl-3-alkali metal (or alkaline earth metal) oxycarbonyl-4'-nitrophenyl ether with a halo substtuted compound in the presence of an inert solvent, such as dimethyl formamide, dimethyl sulfoxide, sulfolane, methylethyl ketone, and the like at a temperature in the range of from about 20° to about 150° C. for a period of time in the range of from about ¼ to about 6 hours. The following equation illustrates this process:

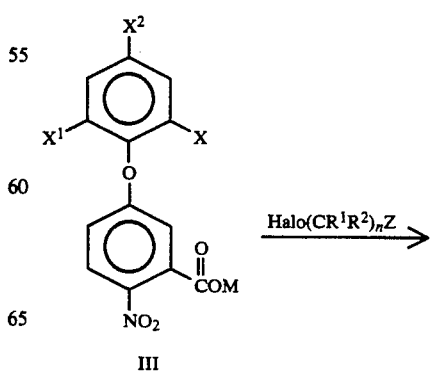

-continued

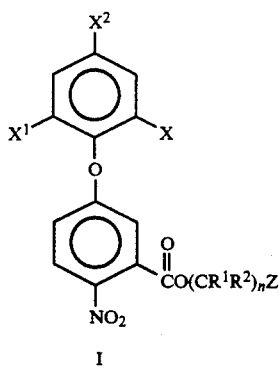

wherein X, $X^1$, X"$R^1$, $R^2$, n, z and halo are as defined above and M is a cation derived from an alkali or alkaline earth metal.

The third process comprises treating an appropriately substituted phenoxide with an appropriately substituted -halo-2-nitrobenzene. The following equation illustrates this process:

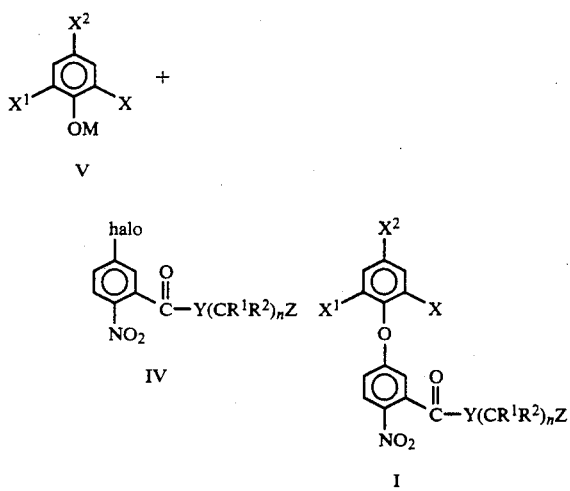

wherein X, $X^1$, $X^2$, Y, $R^1$, $R^2$, n, Z and M are as defined above and halo is chloro, fluoro, bromo and the like. The reaction is generally conducted at a temperature in the range of from about 50° to about 150° C. for a period of time from about 1 to about 96 hours. Solvents which may be employed include dimethyl sulfoxide, dimethyl formamide, sulfolane, methyleethyl ketone, and the like.

Process comprises treating 4-substituted phenyl-3-alkali metal (or alkaline earth metal)oxycarbonyl phenyl ether with a halo substituted compound as described in the Second Process, supra, followed by nitration employing as the nitrating agent, nitric acid, nitric acid/sulfuric acid, nitroniumtetrafluoroborate, nitronium hexafluorophosphate, acetylnitrate and the like. Solvents, if employed include sulfolane, acetic anhydride (acetyl nitrate) and the like at a temperature in the range of from about 20° to about 200° C. and preferably in the range of from about 50° to about 150° C. for a period of time in the range of from ½ hour to 6 hours. The following equation illustrates this process.

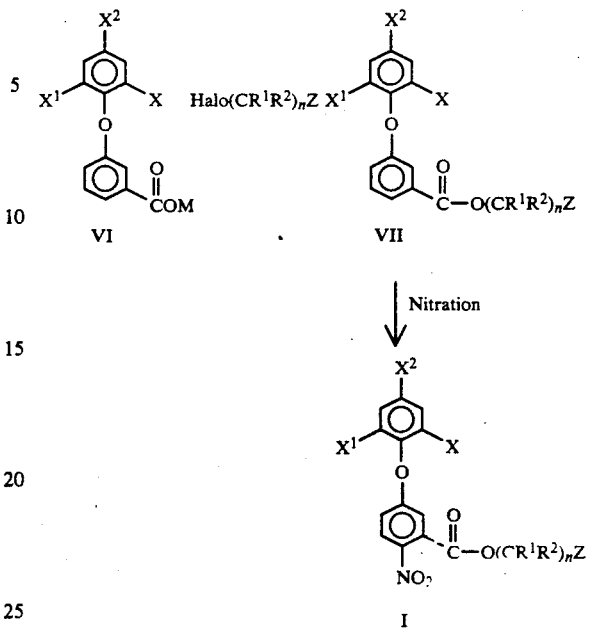

wherein X, $X^1$, $X^2$, $R^1$, $R^2$, n, Z and halo are as defined above.

The diphenyl ethers (I, supra) of the invention are useful as preemergence and postemergence herbicides. Preemergence herbicides are ordinarily used to treat the soil by application either before seeding, during seeding, or after seeding and before the crop emerges. Postemergence herbicides are those which are applied after the plants have emerged and during their growth period. The compounds of this invention are especially active as postemergence herbicides.

Among the crops on which the diphenyl ethers of the invention can be advantageously employed are, cotton, soybeans, peanuts, beans, peas, carrots, corn, wheat, and other cereal crops.

The diphenyl ethers (I, supra) are useful for controlling weeds in rice crops. When used in transplanted rice crops, the ethers can be applied either preemergence or postemergence to the weeds —that is, they can be applied to the transplanted rice plants and their growth medium either before the weed p ants have emerged or while they are in their early stages of growth. The ethers can be applied to the growth medium either before or after the rice has been transplanted to that medium.

The diphenyl ethers (I, supra) can be applied in any amount which will give the required control of weeds. A standard rate of application of the herbicdes of the invention is in the range from about 0.02 to about 12 pounds of diphenyl ether per acre. A preferred range is from about 0.1 to about 2 pounds per acre.

Under some conditions, the diphenyl ethers (I, supra) may be advantageously incorporated into the soil or other growth medium prior to planting a crop. This incorporation can be by any convenient means, including simple mixing with the soil, applying the diphenyl ether to the surface of the soil and then disking or dragging into the soil to the desired depth, or by employing a liquid carrier.

The diphenyl ethers of the invention can be applied to the growth medium or to plants to be treated either neat or as a component in a herbicidal composition or formulation which also comprises an agronomically acceptable carrier. "Agronomically acceptable carrier" is any carrier which can be used to dissolve, disperse or diffuse a herbicidal compound in the composition without impairing the effectiveness of the herbicidal compound and which by itself has no permanent detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in post-emergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

Examples of solvents which are useful in the practice of this invention include alcohols, ketones, aromatic hydrocarbons, dimethyl formamide, dioxane, dimethyl sulfoxide, and the like. Mixtures of these solvents can also be used. The concentration of the solution can vary from about 2% to about 98% of active product with a preferred range being from about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually from about 10% to 60% and in flowable emulsion concentrates, can be as high as about 75%.

Wettable powders suitable for spraying, can be prepared by admixing the compound with a finely divided solid, such as clays, inorganic silicates and carbonates, and silicas and then incorporating wetting agents, sticking agents, and/or dispersing agents. The concentration of active ingredients in such formulations is usually in the range of from about 20% to about 98%, and, preferably, from about 40% to about 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to about 1% to about 10% use concentration.

Granular formulations can be prepared by impregnating a solid, such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of from 16 to 60 mesh. The diphenyl ether will usually comprise from about 2 to about 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Salts and Ester Derivatives Thereof 2,3,6-trichlorobenzoic acid, 2,3,5,6-tetrachlorobenzoic acid, 2-methoxy-3,5,6-trichlorobenzoc acid, 2-methoxy-3,6-dichlorobenzoic acid, 2-methyl-3,6-dichlorobenzoi acid, 2,3-dichloro-6-methylbenzoc acid, 2,4-dichlorophenoxyacetic acid, 2-methyl-4-chlorophenoxyacetic acid, 2-(2,4,5-trichlorophenoxy)propionic acid, 4-(2,4-dichlorophenoxy)butyric acid, 4-(2-methyl-4-chlorophenoxy)butyric acid, 2,3,6-trichlorophenylacetic acid, 3,6-endoxohexahydrophthalic acid, dimethyl 2,3,5,6-tetrachloroterephthalate, trichloroacetic acid, 2,2-dichloropropionic acid, 3-amino-2,5-dichlorobenzoic acid, 2,3-dichloroisobutyric acid.

Carbamic Acid Derivatives ethyl N,N-di(n-propyl)thiocarbamate, propyl N,N-di-acid, (n-propyl)thiocarbamate, ethyl N-ethyl-N-(n-butyl)thiocarbamate, ethyl N-ethyl-N-(n-butyl)thiocarbamate, propyl N-ethyl-N-(n-butyl)thiocarbamate, 2-chloroallyl N,N-diethyldithiocarbamate, N-methyldithiocarbamic acid salts, ethyl 1-hexamethyleneiminecarbothiolate, isopropyl N-phenylcarbamate, isopropyl N-(m-chlorophenyl)carbamate, 4-chloro-2-butynyl N-(m-chlorophenyl)carbamate, methyl N-(3,4-dichlorophenyl)carbamate, methyl-m-hydroxcarb-anilate-m-methylcarbanilate, S-(4-chlorobenzyl)-N,Ndiethylthiolcarbamate.

Phenols dinitro-o-(sec-butyl)phenol and its salts, pentachlorophenol and its salts

Substituted Ureas 3-(3,4-dichlorophenyl)-1,1-dimethylurea, 3-phenyl-1,1-dimethylurea, 3-(3,4-dichlorophenyl)-3-methoxy-1-dimethylene, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, phenyl)-1,1-diethylurea, dichloral urea, N'[4-[2-methylphenyl)ethoxy]phenyl]-N-methoxy-N-methylurea, 1,1,3-trimethyl-3-(5-p-chlorobenzylthio-1,3,4-thia-diazol-2-yl)urea, 3-[-chlorophenoxy)phenyl]-1,1 -dimethylurea.

Substituted Triazines 2-chloro-4,6-bis(ethylamino)-s-triazine, 2-chloro 4-ethylamino-6-isopropylamino-s-triazine, 2-chloro-4,6-bis(methoxypropylamino)-s-triazine, 2-methoxy-4,6-bi(isopropylamino)-s-triazine, 2-chloro-4-ethylamino-6-(3-methoxypropylamino)-s-triazine, 2-methylmercapto-4,6(ethylamino)-s-triazine, 2-methylmercapto-4-ethylamno-6-isopropylamino-s-triazine, 2-chloro-4,6-bis(isoropyl-amino)-s-triazine, 2-methoxy-4,6-bis(ethylamino)-s triazine, 2-methoxy-4-ethylamino-6-isopropylamino-triazine, 2-methylmercapto-4-(2-methoxyethylamino)-6-isopropylamino-s-triazine.

Diphenyl Ether Derivatives 2,4-dichloro-4'-nitrodiphenyl ether, 2,4,6-triOchlorophenyl ether, 2,4-dichloro-6-fluoro-4'-nitrodiphenyl ether 2,-chloro-4-trifluoromethyl-3'-carboxy-4'-nitrodiphenyl ether and its salt and ester derivatives, 3-methyl-4'-nitrodiphenyl ether, 3,5-dimethyl-4'-nitrodiphenyl ether, 2,4'-dinitro-4-trifluoromethyldiphenyl ether, 2,4-dichloro-3'- methoxy-4'-nitrodiphenyl ether, sodium 5-(2-chloro-4-trifluoromethyl-phenoxy)-2-nitrobenzoate.

Anilides

N-(3,4-dichlorophenyl)propionamide, N-(3,4-dichlorophenyl)methacrylamide, N-(3-chloro-4-methylphenyl)-2-methylpentanamide, N-(3,4-dichlorophenyl)trimethylacetamide, N-(3,4-dichlorophenyl)-$\beta,\beta$-dimethylvaleramide, N-isopropyl-N-phenylchloroacetamide, N-n-butoxymethyl-N-(2,6-diethylphenyl)chloroacetamide and N-n-methoxy-methyl-N-(2,6-diethylphenyl)chloroacetamide, 2-chloro-N-(2-ethyl-6-methylphenyl)-N-(2-methoxy-1-methylethyl)acetamide.

Uracils 5-bromo-3-s-butyl-6-methyluracil, 5-bromo-3-cyclohexyl-1,6-dimethyluracil, 3-cyclohexyl-5,6-trimethylene-uracil, 5-bromo-3-isopropyl-6-methyluracil and 3-tert-butyl-5-chloro-6-methyluracil.

Nitriles 2,6-dichlorobenzonitrile, diphenylacetonitrile, 3,5-dibromo-4-hydroxybenzonitrile, and 3,5-diiodo-4-hydroxybenzonitrile.

Other Organic Herbicides b 2-chloro-N,N-diallylacetamide, N-(1,1-dimethyl-2-propynyl)-3,5-dichlorobenzamide, maleic hydrazide, -amino-1,2,4-triazole, monosodium methanearsonate, N,N-diallyl-2-chloroacetamide, disodium methanearsonate, N,N-dimethyl-$\beta,\beta$-diphenylacetamide, N,N-di(n-propyl)-2,6-4-methylaniline, N,N-di(n-propyl)-2,6-dinitro 4-methylsulfonylaniline, $N^3,N^3$-di-n-propyl-2,4-dinitro-6-trifluoromethyl-m-phenylenediamine, 3,5-dinitro-$N^4$, $N^4$-dipropylsulfanilamide, 4-isopropyl-2,6-dinitro-N,N-dipropylaniline, N-[2-chloroethyl)-2,6-dinitro-N-propyl-4-trifluoromethylaniline, 0-(2,4-dichlorophenyl)-0-methylisopropylphosphoramidothioate, 4-amino-3,5,6-trichloropicolinic acid, 2,3-dichloro-1,4-naphthoquinone, di-(methoxythiocarbonyl)disulfide, 3-isopropyl-1H-2,1,3-benzothiadiazine(4)3H-one-2,2,dio oxide,6,7-dihydrodipyridol-[1,2-a:2',1'-c]pyrazidinium salts, 1,1'-dimethyl-4,4'-bi-pyridinium salts and 3,4,5,6-tetrahydro-3,5-dimethyl-2-thio-2H-1,3,5-thiadiazine, 2-($\alpha$-naphthoxy)-N-diethylacetamide, 2-N-(1-napthylaminocarbonyl)benzoic acid, 3-isopropyl-1H-2,1,3-beno-thiadiazin-4(3H)-one 2,2-dioxide, methyl-2-4-(4-chlorophe propionate, methyl-2-4-(3,5-dichloro-pyrid-2-yl)phenoxy]propionate, 2-[1-(allyloxyamino)-propylidene]4-carbomethoxy-5,5-dimethylcylohexane-1, 3-dione.

When mixtures of herbicides are employed, the relative proportions which are used will depend upon the crop to be treated and the degree of selectivity in weed control desired.

EXAMPLE 1

2-Chloro-4-trifluoromethyl-3'-(carbo-tert-butoxycarbonyl-methoxycarbonyl)-4'-nitrodiphenyl ether 2-Chloro-4-trifluoromethyl-3-carboxy-4'-nitrodiphenyl ether (46.2 grams; 0.128 moles) is dissolved in dimethyl sulfoxide (100 ml.) Potassium carbonate (17.7 grams; 0.128 moles) is added and the reaction mixture heated with stirring to 60° C. The reaction mixture is then cooled to 15° C. and allowed to warm to room temperature. Tert-butyl bromoacetate is then added and the reaction mixture stirred at room temperature for one hour. The reaction is repeated substantially as stated above and the two reactions combined and diluted with ether, the ether extract is washed with water then 1% sodium hydroxide solution and finally 5% sulfuric acid solution. The ether solution is then dried over magnesium sulfate. The ether solution is filtered through activated silica gel and the ether evaporated to afford 104.8 grams of 2-chloro-4-trifluoromethyl-3'-(carbo-tert-butoxy-methoxycarbonyl)-4'-nitrodiphenyl ether which after recrystallization from hexane at 0° C. had a m.p. of 25° C. Elemental analysis: Found C, 50.13; H, 3.51; N, 2.87; Cl, 7.38; F, 12.30. $C_{20}H_{17}ClF_3NO_7$ requires C, 50.49; H, 3.60; N 2,94; Cl, 7.45; F, 11.98.

EXAMPLE 2

2-Chloro-4-trifluoromethyl-3'-(carboxymethoxycarbonyl) 4'-nitrodiphenyl ether

2-Chloro-4-trifluoromethyl-3'-tert-butoxycarbonyl-methoxycarbonyl-b 4'-nitrodiphenyl ether (12.0 grams) is heated in an oil bath to 165° C. until bubbling ceased. The product is dissolved in ether, extracted into 5% potassium carbonate, the extract acidified with 5% sulfuric acid and extracted with ether. The ether extract is dried over magnesium sulfate filtered through activated silica gel and the ether removed to afford 9.9 grams of 2-chloro -4-trifluoromethyl-3'(carboxymethoxycarbonyl)-4'-nitrodiphenyl ether. A later sample crystallized and was recrystallized from toluene/hexane, m.p. 103.5°–106° C. Found, 45.99; H, 2.59; N, 2.88; Cl, 8.00; F, 13.02; $C_{16}H_7ClF_3NO_7$ requires C, 45.79; H, 2.16; N, 3.34; Cl, 8.45; F, 13.58.

EXAMPLE 3

2,4-Dichloro-3'-(tert-butoxycarbonylmethoxycarbonyl)-4'-nitrodiphenyl ether

A mixture of 2,4-dichloro-3'-carboxy-4'-nitrodiphenyl ether (20.7 grams), potassium carbonate (9.7 grams) and dimethyl sulfoxide (30 ml.) is heated to 50° C. for 10 minutes and then cooled to 30° C. Tert-butyl bromoacetate is then added followed by an additional 5 m, of dimethyl sulfoxide. The temperature of the reaction mixture rises to 35° C. and the mixture turns yellow. The reaction mixture is stirred for one hour and let stand overnight at room temperature. The reaction mixture is poured into water and extracted with 300 ml. of diethyl ether. The ether solution is washed with water and then with 5% sulfuric acid and then with 5% sodium hydroxde. The ether solution is dried over magnesium sulfate and filtered. Removal of the ether affords 15 grams of the yellow-green oil which is dissolved at hot hexane and allowed to crystallize. Filtration affords 10.5 grams of 2,4-dichloro-3'-(tert-butoxycarbonylmethoxycarbonyl)-4'-nitrodiphenyl ether as yellow-white crystals, melting point 69°–72° C.

EXAMPLE 4

2,4-Dichloro-3'-(carboxymethoxycarbonyl)-4'-nitrodiphenyl ether 2,4'Dichloro-3'-(tert-butoxycarbonylmethoxycarbonyl)-4'-nitrodiphenyl ether (16 grams) is heated at 160°–170° 90 minutes to afford a very viscous fluid orange-brown in color. The product is extracted with diethyl ether (200 ml.) and washed with potassium carbonate solution. The aqueous phase is acidified with 5% sulfuric acid and extracted with ether. The ether solution is dried, filtered and the ether removed to afford 13.4 grams of crude product as a yellow oil. This material was dissolved in 200 cc's of carbon tetrachloride and hexane and allowed to cool. Filtration afforded 11.9 grams of substantially pure 2,4-dichloro-3'-(carboxymethoxy-4'-nitrodiphenyl ether, melting point 93°–95° C. Infrared spectral analysis and NMR analysis confirm the structure.

EXAMPLE 5

2-Chloro-4-trifluoromethyl-3'-(1-carbomethoxyethoxycarbonyl)-4'-nitrodiphenyl ether 2-Chloro-4-trifluoromethyl-3'-carboxy-4'-nitrodiphenyl ether (10.0 grams; 0.028 moles) is dissolved in methylethyl ketone (150 ml.) and potassium carbonate (3.9 grams; 0.028 moles) is added. The solution is heated with stirring to reflux and a white solid preciptates. The solution is cooled to room temperature and methyl bromopropionate is added. The reaction mixture is heated to 75° C. for approximately 3 hours. (Note that during this period an additional one gram of methyl bromopropionate had been added.) The reaction mixture is diluted with ether and the aqueous layers separated and discarded. The ether extract is washed with 5% sulfuric acid and then 1% sodium hydroxide solution. The ether is dried with magnesium sulfate, filtered through silica gel and the ether removed to afford 8.3 grams of 2-chloro-4-trifluoro-methyl-3-(1-carbomethoxyethoxycarbonyl)-4'-nit ether as an oil.

EXAMPLE 6

2-Chloro-4-trifluoromethyl-3'-[1-(carboethoxy)ethoxycarbonyl]-4'-nitrodiphenyl ether To a solution of 2-chloro-4-trifluoromethyl-3'-chlorocarbonyl-4'-nitrophenyl ether (9.0 grams; 0.0236 mole) in 1,2-dimethoxyethane (25 ml.) in a 50 ml. round bottom flask is added ethyl lactate (2.8 grams; 0.0236 moles) at room temperature. Pyridine (1.58 grams; 0.0236 mole) is also added. The reaction mixture is stirred over the weekend at room temperature, and then heated to 75° C. for about 24 hours. The reaction mixture is filtered to remove solid and the filtrate concentrated to afford 12 grams of a yellow oil. The yellow oil is chromatographed over 100 grams of silica gel using toluene as the solvent to give 3.5 g of 2-chloro-4-trifluoromethyl-3'-(1-carboethoxy)ethoxycarbonyl-4'-ntrodiphenylether as yellow oil of 74% purity contaminated with a second product.

EXAMPLE 7

2-Chloro-4-trifluoromethylphenyl-3'-2[(N,N-dimethylamno)ethoxycarbonyl]-4'-nitrophenyl ether

Step A - Potassium 2-chloro-4-trifluoromethyl-phenoxide

2-Chloro-4-trifluoromethylphenol (1.96 grams; 0.010 mole) is dissolved in dimethyl sulfoxide (15 ml.) and The reaction mixture is stirred at room temperature overnight to afford potassium 2-chloro-4-trifluoromethylphenoxide.

Step B - 2-Chloro-4-trifluoromethylphenyl-3'-2[(N,N-dimethylamino)ethoxycarbonyl)-4'-nitrophenyl ether To the product of Step A is added 5-fluoro-2-nitro-(N,N-dimethylaminoethoxycarbonyl)benzene. The reaction mixture is stirred at room temperature for 3 hours and then warmed to 45° for about 18 hours. The reaction mixture is poured into carbon tetrachloride (100 ml.) and extracted with two portions of water (2 × 50 ml.). The carbon tetrachloride layer is dried over anhydrous sodium sulfate, filtered and the solvent removed under vacuum to afford 2.8 grams of 2-chloro-4-trifluoromethylphenyl-3'-2-[(N,N-dimethylamino)ethoxycarbonyl]-4'-nitrophenyl ether. Recrystallization from benzene/hexane afforded substantially pure product having a melting point of 70°–71.5° C. Elemental analysis for: Found C, 48.94, H, 3.74 N, 6.18 Cl, 8.14 F, 13.58 $C_{18}H_{16}HlF_3N_2O_5$ requires C, 49,95 H, 3.73 N, 6.47 Cl, 8.19 F, 13.14

In a manner similar to that described in Examples 1 or 5 all of the diphenyl ethers of this invention may be obtained. Thus by substituting the appropriately substituted halo compound or hydroxy compound for the tert-butyl bromoacetate or ethyl lactate of Examples 1 and 5, respectively, and by following substantially the procedures described in Examples 1 and 5, respectively, the diphenyl ether products of this invention may be obtained. The following equation illustrates the reaction of Examples 1 and 5 and taken together with Table 1 depcit the starting materials and products obtained thereby.

TABLE I

| Ex. No. | X | $X^1$ | $X^2$ | Y | A | $A^1$ | $R^1$ | $R^2$ | n | Z |
|---|---|---|---|---|---|---|---|---|---|---|
| 8 | Cl | H | $CF_3$ | S | Cl | SH | H | H | 1 | $CO_2Me$ |
| 9 | Cl | H | $CF_3$ | NH | Cl | $NH_2$ | H | H | 1 | $CO_2Me$ |
| 10 | Cl | H | $CF_3$ | O | OK | Cl | H | H | 2 | $CO_2H$ |
| 11 | Cl | H | $CF_3$ | O | OK | Br | H | H | 3 | $CO_2Et$ |
| 12 | Cl | H | $CF_3$ | O | OK | Br | $-CH_2\phi$ | H | 1 | $CO_2Me$ |
| 13 | Cl | H | Cl | O | OK | Br | $-CH_2\phi$ | H | 1 | $CO_2Me$ |
| 14 | Cl | H | Cl | O | OK | Br | H | H | 1 | $CO_2$-t-Bu |

EXAMPLE 15

2-Chloro-4-trifluoromethyl-3'-(1-carboethoxy)isopropoxycarbonyl-4'-nitrodiphenyl ether 2-Chloro-4-trifluoromethyl-3'-carboxy-4'-nitrodiphenylether (9.04 g.) and anhydrous potassium carbonate (6.91 g.) in DMSO (30 ml.) were heated to 75° C. and ethyl α-bromoisobutyrate (4.9 g.) in DMSO (10 ml) was added and heating continued for 2 hours at 80°–82° C., at which point additional ethyl α-bromoisobutyrate (0.5 g.) was added. After two additional hours of heating, the mixture was cooled, and diluted with ether. The ether solution was washed with 5% $H_2SO_4$, and 1% NaOH solutions, dried over magnesium sulfate, filtered through activated silica gel, and thoroughly stripped, finally at 0.5 mm/60°–65° C. to remove unreacted bromoester. The residue solidified to a yellow powder which was recrystallized from hexane to afford the desired ester, yield 1.8 g., m.p. 92°–94.5° C. Found C, 50.15; H, 3.54; N, 2.89; Cl, 7.54; F, 11.85. $C_{20}H_{17}ClF_3NO_7$ requires C, 50.45; H, 3.60; N, 2.94; Cl, 7.45; F 11.98.

EXAMPLE 16

2-Chloro-4-trifluoromethylphenyl-3'-[1-(carbo(2-methoxy)ethoxy)ethoxycarbonyl]-4'-nitrophenyl ether A suspension of 2-chloro-4-trifluoromethyl-3'– carboxy-4'-nitrodiphenylether (7.1 g.) in thionyl chloride (2.5 g.) is heated for 1 hour at 110° C. then excess thonyl chloride stripped off under reduced pressure. 2-Methoxyethanol (40 ml.) is added and the mixture heated briefly to 95° C. to form a solution. Excess reagent is removed under reduced pressure and the residue taken up in ether and the solution washed with water and potassium carbonate solution, dried, filtered through activated silica gel, and stripped to yield the desired ester (7.5 g.) as a yellow oil. Found: C, 48.40; H, 3.13; Cl, 8.01; F, 12.13; N, 3.62. $C_{19}H_{15}ClF_3NO_8$ requires C, 47.76; H, 3.16; Cl, 7.42; F, 11.93; N, 2.93.

EXAMPLE 17

2-Chloro-4-trifluoromethyl-3'-(carbotrifluoroethoxy)-methoxycarbonyl-4'-nitrodiphenyl ether.

This compound is prepared from 2-chloro-4-trifluoromethyl-3'-(carboxymethoxycarbonyl)-4'-nitrodiphenyl ether and trifluoroethanol followingsubstantally the procedure of Example 16.

EXAMPLE 18

2-Chloro-4-trifluoromethyl-3'-carbomethoxymethoxycarbonyl-4'-nitrodiphenyl ether.

The potassium salt of 2-chloro-4-trifluoromethyl-3-carboxy-4'-nitrodiphenyl ether is prepared by dissolving the acid in methanol and adding an equivalent amount of potassium hydroxide in methanol and evaporating the methanol. The potassium salt is dissolved in dry dimethyl formamide and methyl α-bromoacetate (14.3 grams; 0.09375 mole) is added. The reaction mixture is heated to 120° for 4 hours. The reaction mixture is added to dilute hydrochloric acid and extracted with hexane. The hexane solution is washed until neutral and then filtered through activated silica gel. The solvent is removed to afford 16 grams of 2-chloro-4-trifluoromethyl-3'-carbomethoxymethoxycarbonyl-4'-nitrodipheny ether. m.p. 97°–98° C.

EXAMPLE 19

2-Chloro-4-trifluoromethylphenyl-3'-(carboallyloxymethoxycarbonyl)-4'-nitrophenyl ether.

To a mixture of 2-chloro-4-trifluoromethylphenyl-3'-carboxymethoxycarbonyl-4'-nitrophenyl ether (10.5 grams and potassium carbonate (4.1 gram) in dimethylsulfoxide (30 milliliters) is added allyl bromide (3.0 gram) at 25° C. The temperature increases to 32° C. and a yellow mixture is formed. A sample tested on thin layer chromatography shows a single spot. The yellow mixture is diluted with 300 milliliters of water and extracted with 2×200 milliliter portions of ether. The ether extract is washed with 100 milliliters of 5% potassium carbonate solution. The ether solution is dried over magnesium sulfate, filtered through activated silica gel and the ether removed to afford 10.3 grams of yellow oil which solidifies. The solid is recrystallized from hexane to afford substantially pure 2-chloro-4-trifluoromethylphenyl-3'-(carboallyloxymethoxycarbonyl)-4-nitrophenyl ether, m.p. 51°–53° C. Found C, 49.94; H, 2.86; Cl, 7.97; F, 12.49; N 2.99; $Cl_{19}H_{13}ClF_3NO_4$ requires C, 49.63; H, 2.85; Cl, 7.71; F, 12.40; N, 3.05.

EXAMPLE 20

2-Chloro-4-trifluoromethylphenyl-3'-(N-dimethyl)carbamylmethoxycarbonyl]-4'-nitrophenyl ether To a well stirred mixture of an aqueous solution of dimethylamine (40% aqueous; 20 milliliters) and diethyl ether (100 milliliters) is added dropwise 2-chloro-4-trifluoromethylphenyl-3'-chlorocarbonylmethoxycarbonyl-4'-nitrophenyl ether. The aqueous phase becomes clear yellow. The reaction mixture is stirred for 20 minutes, the aqueous phase discarded and the yellow ether solution is washed with 5% sulfuric acid and then a 5% potassium carbonate solution. The ether solution is dried over magnesium sulfate and filtered through activated silica gel. A precipitate forms which after standing and cooling is collected. The filtrate is stripped and the crystals which form are collected and combined with the first crop to afford 4.3 grams of substantially pure 2-chloro-4-trifluoromethylphenyl-3 -[(N-dimethyl)carbamylmethoxycarbonyl]-4-nitrophenyl ether, m.p. 108.5°–110° C. Found C, 48.43; H, 3.07; Cl, 8.29; F, 13.27; N, 6.22. $C_{18}H_{14}ClF_3N_2O_6$ requires C, 48.38; H, 3.16; Cl, 7.94; F, 12.76; N, 6.27.

EXAMPLE 21

2,4-Dichloro-3'-carbomethoxymethoxycarbonyl-4'-nitrodiphenyl ether

A mixture of 2,4-dichloro-3-carboxy-4'-nitrodiphenyl ether (14.8 grams), potassium carbonate (8.2 grams) and dimethyl sulfoxide (30 milliliters) is warmed to 50° C. and then cooled to 33° C. at which point methyl bromoacetate is added dropwise The reaction temperature increases to 45° C. The reaction mixture is stirred for an additional hour and then ether and water is added. The ether solution is washed with 5% sulfuric acid, 5% sodium carbonate solution and 10% sodium hydroxide solution then dried over magnesium sulfate, filtered through activated silica gel and stripped to afford 14.5 grams of a yellow green oil. The oil is dissolved in 300 milliliters of isopropanol at 35° C. After cooling, crystals are collected and dried to afford 11.5 grams of 2,4-Dichloro-3'-carbomethoxy-methoxycarbonyl-4'-nitrodiphenyl ether as yellow white needles m.p. 53°–55.5° C. Found C, 47.80; H, 2.64; Cl, 18.10; N, 3.72; 0, 27.13. $C_{16}H_{11}Cl_2NO_7$ requires C, 48.02; H, 2.77; Cl, 17.72; N, 3.50; 0, 27.99.

EXAMPLE 22

Sodium salt of 2-Chloro-4-trifluoromethyl-3'-(carboxy-methoxycarbonyl)-4'-nitrodiphenyl ether To a suspension of 2-chloro-4-trifluoromethyl-3'-(carboxymethoxycarbonyl)-4'-nitrodiphenyl ether (2.1 g.) in water (1,000 ml.) s slowly added dropwise over a 90 minute period a solution of sodium hydroxide (9.5 ml. of 0.5 N diluted to 50 ml.). The reaction mixture is stirred for an additional 90 minutes and then filtered to remove undissolved starting materials. The water is removed under high vacuum at 30° C.–40° C. to afford 1.0 g. of 2-chloro-4-trifluoromethyl-3'-(carboxymethoxycarb-onyl)-4'-nitrodiphenyl ether, sodium salt.

(a) By following substantially the procedure described in Example 22 and by substituting for the sodium hydroxide recited therein an equal molar quantity of potassium hydroxide there is obtained 1.2 g. of the potassium salt of 2-chloro-4-trifluoromethyl-3'-(carboxymethoxycarbonyl)-4'-nitrodiphenyl ether.

EXAMPLE 23

Lithium salt of 2-Chloro-4-trifluoromethyl-3'-(carboxy-methoxycarbonyl)-4'-nitrodiphenyl ether To a solution of 2-chloro-4-trifluoromethyl-3'-(carboxymethoxycarbonyl)-4'-nitrodiphenyl ether (2.1 g. 0.005 mole) in diethyl ether (100 ml.) under nitrogen is added n-butyl lithium solution (2.6 cc of a 1.9M solution; 0.0049 mole). The solution turns clear red. After 30 minutes of stirring the solution darkens. The reaction mixture is stirred overnight at room temperature. The solvent is removed to afford 2.4 g. of lithium salt of 2-chloro-4-trifluoromethyl-3'-(carboxy-methoxycarbonyl)-4'-nitrodiphenyl ether as a crystalline brown solid.

EXAMPLE 24

2,4-Dichloro-3'-[1-(methoxycarbonyl)ethoxycarbonyl]-4'-nitrodiphenyl ether

To a solution of 2,4-dichloro-3'-carboxy-4'-nitrodiphenyl ether (8.88 g.; 0.03 moles) in dimethylsulfoxide (30 ml.) is added potassium carbonate (8.29 g.; 0.06 mole). The mixture is heated to 70° C. for 5 minutes and then cooled to 20° C. is added methyl α-bromoproionate (5.01 g.; 0.03 moles) in dimethyl sulfoxide (5 ml.). After stirring the reaction mixture at room temperature for 90 minutes, it is diluted with ether (200 ml.) and washed with water (100 ml.). The ether phase is washed with 5% sulfuric acid and then 10 ml. of 5% sodium hydroxide. The ether solution is dried over magnesium sulfate and then filtered through Bio-sil. Removal of the ether affords 9.9 g. of 2,4-dichloro-3'-[1-(methoxycarbonyl)ethoxycarbonyl]-4'-nitrodiphenyl ether as a yellow oil.

EXAMPLE 25

2-Chloro-4-trifluoromethyl-3'-[α-(methoxycarbonyl)-'-(phenyl)ethoxycarbonyl]-4'-nitrodiphenyl ether To a stirred mixture of 2-chloro-4-trifluoromethyl-3'-carboxy-4'-nitrodiphenyl ether (10.85 g.; 0.03 moles) in methylethyl ketone (30 ml.) is added potassium carbonate (8.3 g.; 0.06 moles). An immediate reaction with gas evolution occurs leaving a paper-like mass. After warming for 15 minutes at 60° C. the mixture is cooled and methyl α-bromo-α-benzyl acetate (7.3 g.; 0.03 moles) is added. The emulsion is very thick and an additional 80 ml. of methylethyl ketone s added. The reaction mixture is allowed to stand overnight and then stirring is continued. An additional 200 ml. of methylethyl ketone is added and the reaction mixture is heated to 60° C. for 3 hours. The reaction mixture is cooled and diluted with diethyl ether (200 ml.). The ether solution is washed with water (200 ml.) and then with 5% sulfuric acid and, finally, with 5% potassium carbonate. The ether solution is dried over molecular sieves. The ether solution is filtered through activated silica gel and the ether removed to afford 8.3 g. of a yellow oil. Thin layer of chromatography indicates a substantial amount of unreacted ester. The yellow oil is diluted with methylethyl ketone (70 ml.) and an additional quantity of the nitrodiphenyl ether (7.2 g.; 0.02 moles) and potassium carbonate (3.4 g.; 0.02 moles) is added and the mixture heated to reflux and refluxing is continued overnight. The product is extracted with ether and the ether solution is washed with water, 5% sulfuric aoid and, finally, 5% potassium carbonate solution. The ether solution is dried over magnesium sulfate, filtered through activated silica gel and the ether removed to afford 1.9 g. of 2-chloro-4-trifluoro-methyl-3'-[α-(methoxycarbonyl)-α-(phenyl)ethoxyo carbonyl]-4'-nitrodiphenyl ether.

EXAMPLE 26

2-Chloro-4-trifluoromethyl-3'-[α--(methoxycarbonyl) α-(phenyl)methoxycarbonyl]-4'-nitrodiphenyl ether To a mixture of 2-chloro-4-trifluoromethyl-3'-carboxy-4'-nitrodiphenyl ether (7.23 g.; 0.02 moles) methylethyl ketone (25 ml.) is added potassium carbonate (5.52 g.; 0.04 moles). An immediate reaction occurs with gas evolution. An additional 100 ml. of methylethyl ketone is added followed by the addition of methyl α-bromophenyl acetate (4.58 g.; 0.02 moles). The reaction mixture is stirred for 90 minutes and allowed to stand overnight at room temperature. Stirring is continued for an additional 4 hours at room temperature and then the reaction mixture is heated to 65° C. for 3 hours. The reaction mixture is cooled and diethyl ether (300 ml.) is added. The ether solution is washed with water; 5% sulfuric acid and, finally, a 5% potassium carbonate solution. The ether phase is dried over molecular sieves, filtered through activated silica gel and the ether removed to afford 8.5 g. of 2-chloro-4-trifluoromethyl-3'-[α-(methoxycarbonyl)-α-(phenyl)metho -4'-nitrodiphenyl ether as a yellow solid. Recrystallization from isopropanol affords 5.0 g. of fluffy white crystals, m.p. 114°–117° C.

EXAMPLE 27

2-Chloro-4-trifluoromethyl-3'-[(methoxycarbonyl)methylthiocarbonyl]-4'-nitrodiphenyl ether 2-Chloro-4-trifluoromethyl-3'-carboxy-4'-nitrodiphenyl ether (12.6 g.; 0.03 moles) and thionyl chloride (4.2 g.; 2.25 moles) is stirred and heated in a bath at 100° C. The mixture melts and heating is continued at 100° C. for an additional hour. An additional 2 g. of thionyl chloride is added and the mixture heated for 30 additional minutes. The reaction mixture is allowed to stand overnight at room temperature and reheated for 2 hours. The excess thionyl chloride is removed under vacuum and chlorine and oil bath at 100° C. The dark brown oil is cold and diluted with diethyl ether (50 ml.). To this dark solution is added ethyl 2-mercaptoacetate (3.7 g.). The reaction mixture is stirred for 2 hours at room temperature and then allowed to stand for 9 days (fortitutious). The mixture is then diluted with diethyl ether and washed in water. The ether solution is washed with 5% sulfuric acid solution and then a 5% potassium carbonate solution. The ether soluton is dried over magnesium sulfate and then filtered through activated silica gel. Removal of the ether affords 13.1 gram of product. This material is dissolved in diethyl ether (43 ml.) and enough hexane (85 ml.) is added until hazy. This solution is then passed through activated silica gel and the solvent removed to afford 9.1 g. of 2-chloro-4-tri-fluoromethyl-3'-[(methoxycarbonyl)methylthiocarbonyl]-4'-nitrodiphenyl ether as a red oil.

EXAMPLE 28

2-Chloro-4-trifluoromethyl-3-[α(ethoxycarbonyl)propoxycarbonyl]4'-nitrodiphenyl ether A mixture of 2-chloro-4-trifluoromethyl-3-carboxy-4'-nitrodiphenyl ether (10.9 g.; 0.03 moles) in met ketone (50 ml.) is heated for 1 hour at 60°–70° C. and then cooled. Ethyl 2-bromobutyrate (5.9 g.; 0.03 moles) is then added and the emulsion warmed to 50° C. for 2 hours. The mixture is allowed to stand at room temperature overnight. Heating is resumed at 60°–70° C. for an additional 4 hours. Ether (100 ml.) is added and the ether solution washed with water, followed by 5% sulfuric acid solution and, finally, with a 5% potassium carbonate solution. The ether is dried over magnesium sulfate and the ether solution is filtered through activated silica gel. The ether is removed to afford 6.2 g. of 2-chloro-4-trifluoromethyl-3-[α(ethoxy-carbonyl)-propoxycarbonyl]4'-nitro-diphenyl ether. The material is dissolved in hexane (except for some small amount about 0.3 g. of orange oil) and the hexane decanted and removed to afford 5.6 g. of product. This material is redissolved in hexane and passed through 40 g. of activated silica gel in hexane. Three cuts were taken and the last two combined and the hexane removed to afford 2.5 g. of product as a yellow oil.

EXAMPLE 29

2-Chloro-4-trifluoromethyl-3-[N-(1-carboethoxyethyl)-carbo amyl]-4'-nitrodiphenyl ether 2-Chloro-4-trifluoromethyl-3'-carboxy-4'-nitrodiphenyl ether (0.04 moles) and thionyl chloride (5.4 g.; 0.045 moles) are mixed together and refluxed for two hours. 100 ml. of diethyl ether are added to the reaction mixture. This was then added dropwise to a mixture of ethyl L-alanine hydrochloride (6.1 g.; 0.04 moles) and 2,6-lutidine (8.51 g.; 0.08 moles) dissolved in 25 ml. of diethyl ether. The resultant red and black solution was then stirred at room temperature overnight. The black solution is diluted with diethyl ether and then washed with water. The ether solution is then washed in 5% sulfuric acid followed by 5% potassium carbonate solution. The ether is dried over magnesium sulfate and filtered through activated silica gel. Removal of the ether affords a black oil which soon solidifies. The solid is dissolved in hot hexane. The hexane is decanted and allowed to cold. The residual oil is extracted with hexane and the hexane extracts placed in a refrigerator. The first hexane extract affords 0.06 g. of product having a melting point of 45°–47° C. The second extract affords a red black solid glass-like material, 3.9 g. having a melting point of 40°–49° C.

EXAMPLE 30

2-Chloro-4-trifluoromethyl-3'-[α-(ethoxycarbonyl)isobutoxycarbonyl]-4'-nitrodiphenyl ether 2-Chloro-4-trifluoromethyl-3'-carboxy-4'-nitrodiphenyl ether (14.5 g.; 0.04 moles) is dissolved in dimethyl sulfoxide (40 ml.). Potassium carbonate (11.0 g.; 0.08 moles) is added to this mixture. The reaction mixture is then heated to 60° C. The reaction mixture is cooled to room temperature and ethyl 2-bromo-3-methyl-butyrate (8.4 g.; 0.04 moles) in dimethyl sulfoxide (10 ml.) is then added. The reaction mixture is stirred at room temperature and let stand. The reaction mixture is extracted with diethyl ether and the ether solution washed successively with water, 5% sulfuric acid solution and 5% potassium carbonate solution. The ether solution is dried over magnesium sulfate and filtered through activated silica gel. Removal of the ether affords 4.6 g. of 2-chloro-4-trifluoromethyl-3'-[α(ethoxycarbonyl)-iso- butoxycarbonyl]-4'-nitro-dip ether.

EXAMPLE 31

2-chloro-4-trifluoromethyl-3'-[1-(aminocarbonyl)ethoxycarbonyl]-4'-nitrodiphenyl ether 2-chloro-4-trifluoromethyl-3'-carboxy-4'-nitrodi-phenyl ether (30.0 g.) is dissolved in dimethyl sulfoxi (30 ml.) and heated to 80° C. Potassium carbonate (12.6 g.) is then added. Foaming occurs and when the foaming ceases the mixture is cooled in an ice bath to 38° C. α-Bromopropionamide (13.9 g.) is added. The reaction mixture is heated for 1½ hours at 95° C. The reaction mixture is diluted with ether and the ether extract is washed successively with water, 1% sodium hydroxide solution and 5% sulfuric acid. The ether is removed and the residue crystallized from toluene. The toluene solution is filtered crystals form but are not the desired amine. The filtrate is stripped to afford 4.0 g of desired 2-chloro-4-trifluoromethyl-3'-[1-(aminocarbonyl)ethoxycarbonyl]-4'-nitrodiphenyl ether

EXAMPLE 32

2-Chloro-4-trifluoromethyl-3'[9-(carboxy)ethoxycarbonyl]-'-nitrodiphenyl ether

2-Chloro-4-trifluoromethyl-3'-[1-(methoxycarbonyl)-methoxycarbonyl]-4'-nitrodiphenyl ether of Example 5 (47.7 g.; 0.107 moles) is mixed together with -toluenesulfonic acid (1.0 gram), dioxane (180 ml.) and water (5 ml.). The reaction mixture is heated, with stirring, to reflux for 6 hours. The reaction mixture is diluted with 5% sulfuric acid and extracted with ether. The ether extract is itself extracted with 1% sodium hydroxide solution. This base extract is acidified with sulfuric acid and extracted with ether. The first ether extract is dried over magnesium sulfate, filtered through activated silica gel and the ether removed to afford 12.3 g. of 2-chloro-4-trifluoromethyl-3'[1(carboxy)ethoxycarbonyl]-4'-nitrodiphenyl ether.

EXAMPLE 33

Sodium salt of 2-Chloro-4-trifluoromethyl-3'[1-(carb-oxy)ethoxycarbonyl]-4'-nitrodiphenyl ether The acid of Example 32 (2.2 g.) is dissolved in methanol (20 ml.). To this solution is added a sodium methoxide (0.27 g.; 0.005 mole) in methanol (20 ml.). The reaction mixture is stirred for 10 minutes and the methanol removed. The product is extracted with ether and the ether removed to afford 2.1 g. of the sodium salt of 2-chloro-4-trifluoromethyl-3'[1-(carboxy)-ethoxycarbonyl]-4'-nitrodiphenyl ether.

EXAMPLE 34

Potassium salt of 2-Chloro-4-trifluoromethyl-3'[1-(carboxy)ethoxycarbonyl]-4'-nitrodiphenyl ether The product of Example 32 (2.2 g.) is dissolved in methanol. To this solution is added a solution of potassium hydroxide (0.28 g.) in methanol (20 ml.). The reaction mixture is stirred for 10 minutes and the methanol removed under vacuum. The product is extracted with ether and the ether removed to afford 2.1 of 2-chloro-4-trifluoromethyl-3'[1-(carboxy)ethoxy carbonyl]-4'-nitrodiphenyl ether, potassium salt, m.p. 100°–105° C.

EXAMPLE 35

2-Chloro-4-trifluoromethyl-3'-[α-(ethoxycarbonyl)-α-methylethoxycarbonyl]-4'-nitrodiphenyl ether A mixture of 2-chloro-4-trifluoromethyl-3'-chlorocarbonyl-4'-nitrodiphenyl ether (10 g.); ethyl 3(3.5 g.) and lutidine (2.8 g.) in toluene (15 ml.) is heated with stirring to 55° C. Heating is continued for two days (fortitutious). The reaction mixture is diluted with water and extracted with ether. The ether solution is washed with a 5% sodium carbonate solution and then water. The ether solution is then dried over magnesium sulfate filtered through charcoal and activated silica gel and the solvent removed to yield 8.2 g. of 2-chloro-4-trifluoro-methyl-3'-[α-(ethoxycarbonyl)- α-methylethoxycarbony 4'-nitrodiphenyl ether as an oil.

EXAMPLE 36

2-Chloro-4-trifluoromethyl-3'-(carboethoxybutoxycarb-onyl)-4'-nitrodiphenyl ether 2-Chloro-4-trifluoromethyl-3'-carboxy-4'-nitrodiphenyl ether (10.85 g, 0.03 moles) is dissolved in methylethyl ketone (30 ml.) and potassium carbonate (8.3 g; 0.06 moles) added. A solid forms. Additional methyl ethyl ketone (40 ml) is added and the emulsion heated in an oil bath at 100° C. and then cooled in an ice bath. Ethyl 5-bromovalerate (6.27 g; 0.03 ml) is added and also additional methylethyl ketone (10 ml) to maintain slurring. The reaction mixture is heated to 60° C. for 5 minutes, cooled and stirred at room temperature for 2 hours at room temperature. The mixture is colored pinkpurple. The emulsion is dilute with either and the ether solution washed with water, 5% sulfuric acid solution and then 5% potassium carbonate. The ether solution is dried over magnesium sulfate and filtered through activated silica gel. The ether is removed to afford 8.0 g. of yellow oil NMR shows impurity of ethyl 5-bromovalerate which is removed by distillation. The residue is 2.5 g of 2-Chloro-4-trifluoromethyl-3'-(carboethoxybutoxycarbonyl)-4'-nitrodiphenyl ether. NMR and IR confirm product.

EXAMPLE 37

2-Chloro-4-trifluoromethyl-3'-carboethoxymethoxycar-bonyl-4'-nitrodiphenyl ether To a 12 1, 4-necked round bottom flask is added 2-chloro-4-trifluoromethyl-3'-carboxy-4'-nitrodiphenyl ether (2713 g; 7.5 moles) in methylethyl ketone (MEK) (6.6 1) under a nitrogen atmosphere. Heated to 79° C. (collected 100 ml of MEK). Cooled to 40° C. and removed 3700 ml of solution. Added potassium carbonate (250 gl in about 3 to 5 minutes —to fast as violent foaming occurred causing a loss of 2.5 to 3.1 of material. Added MEK (800 ml). Heated to 60° C. and continued addition of potassium carbonate (807 g; total 1057 g, 7.65 moles). Stirred overnight at a temperature of about 40° C. Heated to 70° C. and added ethyl bromoacetate (1466 g; 8.25 moles) over a 2½ hour period. The temperature was increased to distill MEK. (Removed 2200 ml over a 4½ period). The heat was removed and stirring was continued overnight at room temperature. The reaction mixture is washed successively with water (4500 ml), (the water wash is extracted with 6 pints of toluene) 10% sodium carbonate (2500 ml), brine (2500 ml) and water (2500 ml). The MEK solution and toluene are combined, dried over magnesium sulfate, filtered and stripped under vacuum to afford 3347 g of 2-Chloro-4-trifluoromethyl-3'-carboethoxymethoxycarbonyl-4'-nitro ether m.p. 47°-52° C.

Other salts, esters, amides of the acid may be prepared by methods disclosed herein and by other methods known to those skilled in the art and include the alkali metal and alkaline earth metal salts, the mono- and dialkyl amines and the lower alkyl ester derivatives.

One skilled in the art will appreciate that the above examples are merely illustrative and are capable of a wide variation and modification without departing from the spirit of this invention as defined by the following clams.

TEST PROCEDURE

This example shows the herbicidal activity of the diphenyl ethers of the invention exhibited on the following representative species:

|  |  |  | Approximate No. Seeds |
|---|---|---|---|
| Monocots: | Barnyardgrass | (Echinochloa crusgalli) | 25 |
|  | Downybrome | (Bromus tectorum) | 20 |
|  | Foxtail | (Setaria spp) | 25 |
|  | Johnsongrass | (Sorghum halepense) | 25 |
|  | Nutsedge | (Cyperus esculentus) | 5 |
|  | Wild Oat | (Avena fatua) | 20 |
| Dicots: | Cocklebur | (Xanthium pensylvanicum) | 3 |
|  | Marigold | (Tagetes spp) | 15 |
|  | Morning-glory | (Ipomoea spp) | 10 |
|  | Tomato | (Lycopersicon esculentum) | 15 |
|  | Velvetleaf | (Abutilon theophrasti) | 15 |

The following test procedure is employed. Seeds of the above species are planted in soil in trays (approx. 7"×10 ½"×3"). For preemergence tests, the trays are sprayed with the test compound immediately after planting. For postemergence tests, the seeds are allowed to germinate and after growing in the greenhouse for two weeks, the growing plants are treated with the test compound. The compound to be evaluated is dissolved in acetone or water and sprayed over the trays using a carrier volume equivalent to 50 gallons per acre at the rate of appliction (in pounds per acre, lb/A) specified in the table. About two weeks after application of the test compound, the state of growth of the plants is observed and the phytotoxic effect of each compound determined as follows: each species is evaluated on a scale of 0–100 in which 0=no activity and 100=total kill and the result for the monocots and dicots separately averaged. The following table sows the results obtained for the compounds of the invention at 0.5 lb/A. and 2.0 lb/A. except as noted*.

| | Diphenylethers - Herbicidal Activity | | | | | | | |
|---|---|---|---|---|---|---|---|---|
| | Rate 0.5 lb/A | | | | Rate 2.0 lb/A | | | |
| Ex. | Pre | | Post | | Pre | | Post | |
| No. | AM+ | AD+ | AM | AD | AM | AD | AM | AD |
| 1 | 42 | 52 | 10 | 44 | 77 | 98 | 23 | 55 |
| 2 | 62 | 58 | 38 | 93 | 93 | 98 | 57 | 96 |
| 3 | 2 | 4 | 2 | 18 | 5 | 49 | 2 | 22 |
| 4 | 2 | 42 | 33 | 94 | 0 | 20 | 20 | 96 |
| 5 | 48 | 39 | 60 | 92 | 76 | 99 | 68 | 98 |
| 6 | 45 | 58 | 43 | 92 | 83 | 100 | 50 | 98 |
| 11 | 31 | 85 | 37 | 98 | 56 | 100 | 75 | 100 |
| 15 | 42 | 76 | 18 | 80 | 75 | 97 | 25 | 96 |
| 16 | 15 | 38 | 3 | 79 | 70 | 94 | 37 | 100 |
| *17 | 73 | 77 | 43 | 99 | 72 | 92 | 46 | 98 |
| 18 | 55 | 55 | 52 | 100 | 94 | 99 | 75 | 100 |
| 19 | 27 | 44 | 10 | 84 | 90 | 98 | 25 | 95 |
| 20 | 25 | 44 | 2 | 54 | 58 | 82 | 17 | 72 |
| 21 | 0 | 19 | 3 | 63 | 0 | 56 | 7 | 91 |
| 22 | 38 | 46 | 25 | 89 | 88 | 89 | 70 | 100 |
| *22a | 74 | 88 | 53 | 96 | 87 | 99 | 40 | 100 |
| *23 | 76 | 91 | 27 | 96 | 74 | 97 | 31 | 91 |
| 24 | 10 | 4 | 7 | 56 | 7 | 67 | 13 | 80 |
| 25 | 18 | 59 | 5 | 38 | 68 | 72 | 10 | 51 |
| 26 | 34 | 76 | 0 | 24 | 23 | 57 | 0 | 18 |
| 27 | 42 | 36 | 7 | 78 | 78 | 93 | 30 | 94 |
| 28 | 60 | 99 | 42 | 99 | 75 | 100 | 67 | 100 |
| 29 | 13 | 40 | 0 | 78 | 50 | 54 | 0 | 79 |
| 30 | 22 | 92 | 3 | 59 | 40 | 100 | 12 | 79 |
| *32 | 79 | 84 | 28 | 99 | | | | |
| *33 | 64 | 48 | 20 | 98 | | | | |
| *34 | 62 | 58 | 22 | 100 | | | | |
| 35 | 45 | 74 | 35 | 96 | 91 | 99 | 64 | 99 |
| 37 | 48 | 66 | 34 | 95 | 86 | 100 | 58 | 99 |

*1.0 lb/A.
+AM = Average Monocot; AD = Average Dicot

| | | DIPHENYLETHERS - PHYSICAL DATA | | | | |
|---|---|---|---|---|---|---|
| Example # | m.p. | Molecular Formula | C found (reqd) | H found (reqd) | N found (reqd) | Cl found (reqd) |
| 1 | 25° C. | $C_{20}H_{17}Cl_1F_3N_1O_7$ | 50.13 (50.49) | 3.51 (3.60) | 2.87 (2.94) | 7.38 (7.45) |
| 2 | 103.5–106° C. | $C_{16}H_7Cl_1F_3N_1O_7$ | 45.99 (45.79) | 2.59 (2.16) | 2.88 (3.34) | 8.00 (8.45) |
| 3 | 69–79° C. | $C_{19}H_{17}Cl_2N_1O_7$ | 51.87 (51.60) | 3.87 (3.88) | 3.65 (3.17) | 16.50 (16.03) |
| 4 | 93–95° C. | $C_{15}H_9Cl_2N_1O_7$ | 46.52 (46.65) | 2.29 (2.35) | 3.78 (3.63) | 18.40 (18.36) |
| 5 | Oil | $C_{18}H_{13}Cl_1F_3N_1O_7$ | 46.94 (48.29) | 2.90 (2.93) | 2.93 (3.13) | 8.59 (7.92) |
| 6 | Oil | $C_{19}H_{15}Cl_1F_3N_1O_7$ | 49.16 (49.39) | 3.19 (3.27) | 3.31 (3.03) | 8.20 (7.68) |
| 11 | Oil | $C_{20}H_{17}Cl_1F_3N_1O_7$ | 50.66 (50.49) | 3.80 (3.60) | 3.02 (2.94) | 8.27 (7.45) |
| 15 | 92–94.5° C. | $C_{20}H_{17}Cl_1F_3N_1O_7$ | 50.15 (50.45) | 3.54 (3.60) | 2.89 (2.94) | 7.54 (7.45) |
| 16 | Oil | $C_{19}H_{15}Cl_1F_3N_1O_8$ | 48.40 (47.76) | 3.13 (3.16) | 3.62 (2.93) | 8.01 (7.42) |
| 17 | Oil | $C_{18}H_{10}Cl_1F_6N_1O_7$ | 43.78 (43.09) | 2.02 (2.01) | 2.79 (2.79) | 7.04 (7.07) |
| 18 | 97–98° C. | $C_{17}H_{11}Cl_1F_3N_1O_7$ | 45.36 (47.07) | 2.76 (2.56) | 3.26 (3.23) | 9.26 (8.17) |
| 19 | 51–53° C. | $C_{19}H_{13}Cl_1F_3N_1O_4$ | 49.94 (49.63) | 2.86 (2.85) | 2.99 (3.05) | 7.97 (7.71) |
| 20 | 108.5–110° C. | $C_{18}H_{14}Cl_1F_3N_2O_6$ | 48.43 (48.38) | 3.07 (3.16) | 6.22 (6.27) | 8.29 (7.94) |
| 21 | 53–55° C. | $C_{16}H_{11}Cl_2N_1O_7$ | 47.80 (48.02) | 2.64 (2.77) | 3.72 (3.50) | 18.10 (17.72) |
| 22 | — | $C_{16}H_8Cl_1F_3N_1O_7Na$ | 41.72 (43.51) | 1.91 (1.83) | 2.82 (3.17) | 5.32 (8.03) |
| 22a | — | $C_{16}H_8Cl_1F_3N_1O_2K_1$ | 45.15 (41.98) | 2.04 (1.76) | 3.19 (3.06) | 8.66 (7.74) |
| 23 | — | $C_{16}H_8Cl_1F_3N_1O_7Li$ | 45.65 (45.15) | 2.88 (1.89) | 2.80 (3.29) | 7.99 (8.33) |
| 24 | Oil | $C_{17}H_{13}Cl_2N_1O_7$ | 49.17 (49.29) | 3.09 (3.16) | 3.58 (3.38) | 17.74 (17.12) |
| 25 | Oil | $C_{24}H_{17}Cl_1F_3N_1O_7$ | 55.29 (55.02) | 3.41 (3.27) | 2.83 (2.67) | 7.27 (6.77) |
| 26 | 114–117° C. | $C_{23}H_{15}Cl_1F_3N_1O_7$ | 54.28 (54.18) | 2.83 (2.96) | 2.94 (2.75) | 7.02 (6.96) |
| 27 | Oil | $C_{18}H_{13}Cl_1F_3N_1O_6S_1$ | 46.33 (46.60) | 2.72 (2.82) | 2.98 (3.02) | 8.43 (7.44) |
| 28 | Oil | $C_{20}H_{17}Cl_1F_3N_1O_7$ | 52.28 (50.48) | 3.85 (3.60) | 3.01 (2.94) | 7.65 (7.45) |
| 29 | 45–47° C. | $C_{19}H_{16}Cl_1F_3N_2O_6$ | 49.08 (49.52) | 3.06 (3.50) | 5.24 (6.08) | 11.89 (7.70) |

DIPHENYLETHERS - PHYSICAL DATA

| Example # | m.p. | Molecular Formula | C found (reqd) | H found (reqd) | N found (reqd) | Cl found (reqd) |
|---|---|---|---|---|---|---|
| 30 | Oil | $C_{21}H_{19}Cl_1F_3N_1O_7$ | 50.40 (51.45) | 3.82 (3.91) | 3.14 (2.86) | 9.16 (7.24) |
| 31 | Oil | $C_{17}H_{12}Cl_1F_3N_2O_6$ | 51.67 (47.18) | 3.46 (2.80) | 5.58 (6.47) | 8.07 (8.19) |
| 32 | Oil | $C_{17}H_{11}Cl_1F_3N_1O_7$ | 47.23 (47.08) | 2.87 (2.56) | 2.88 (3.23) | 7.59 (8.17) |
| 33 | 105–110° C. | $C_{17}H_{11}Cl_1F_3N_1O_2Na$ | 44.27 (44.81) | 2.14 (2.21) | 3.29 (3.07) | 7.42 (7.78) |
| 34 | 100–105° C. | $C_{17}H_{11}Cl_1F_3N_1O_7K$ | 43.88 (43.28) | 2.59 (2.14) | 2.88 (2.97) | 7.43 (7.51) |
| 35 | Oil | $C_{20}H_{17}Cl_1F_3N_1O_7$ | 53.96 (50.49) | 3.99 (3.60) | 3.05 (2.94) | 7.23 (7.45) |
| 36 | Oil | $C_{21}H_{19}Cl_1F_3N_1O_7$ | 53.46 (51.49) | 4.16 (3.91) | 2.71 (2.86) | 7.38 (7.24) |

The following is a listing of some of the preferred products of this invention.

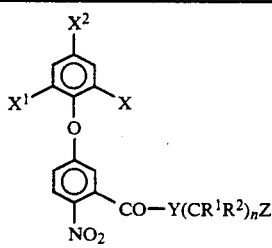

| Example | X | $X^2$ | $X^1$ | Y | $R^1$ | $R^2$ | n | Z |
|---|---|---|---|---|---|---|---|---|
| 1 | Cl | $CF_3$ | H | O | H | H | 1 | $CO_2$-t-Bu |
| 2 | Cl | $CF_3$ | H | O | H | H | 1 | $CO_2H$ |
| 3 | Cl | Cl | H | O | H | H | 1 | $CO_2$-t-Bu |
| 4 | Cl | Cl | H | O | H | H | 1 | $CO_2H$ |
| 5 | Cl | $CF_3$ | H | O | Me | H | 1 | $CO_2Me$ |
| 6 | Cl | $CF_3$ | H | O | Me | H | 1 | $CO_2Et$ |
| 11 | Cl | $CF_3$ | H | O | H | H | 3 | $CO_2Et$ |
| 15 | Cl | $CF_3$ | H | O | Me | Me | 1 | $CO_2Et$ |
| 16 | Cl | $CF_3$ | H | O | H | H | 1 | $CO_2CH_2CH_2OMe$ |
| 17 | Cl | $CF_3$ | H | O | H | H | 1 | $CO_2CH_2CF_3$ |
| 18 | Cl | $CF_3$ | H | O | H | H | 1 | $CO_2Me$ |
| 19 | Cl | $CF_3$ | H | O | H | H | 1 | $CO_2CH_2CH=CH_2$ |
| 20 | Cl | $CF_3$ | H | O | H | H | 1 | $CONMe_2$ |
| 21 | Cl | Cl | H | O | H | H | 1 | $CO_2Me$ |
| 22 | Cl | $CF_3$ | H | O | H | H | 1 | $CO_2Na$ |
| 22a | Cl | $CF_3$ | H | O | H | H | 1 | $CO_2K$ |
| 23 | Cl | $CF_3$ | H | O | H | H | 1 | $CO_2Li$ |
| 24 | Cl | Cl | H | O | Me | H | 1 | $CO_2Me$ |
| 25 | Cl | $CF_3$ | H | O | $CH_2C_6H_5$ | H | 1 | $CO_2Me$ |
| 26 | Cl | $CF_3$ | H | O | $C_6H_5$ | H | 1 | $CO_2Me$ |
| 27 | Cl | $CF_3$ | H | S | H | H | 1 | $CO_2Et$ |
| 28 | Cl | $CF_3$ | H | O | Et | H | 1 | $CO_2Et$ |
| 29 | Cl | $CF_3$ | H | NH | Me | H | 1 | $CO_2Et$ |
| 30 | Cl | $CF_3$ | H | O | i-Pr | H | 1 | $CO_2Et$ |
| 31 | Cl | $CF_3$ | H | O | Me | H | 1 | $CONH_2$ |
| 32 | Cl | $CF_3$ | H | O | Me | H | 1 | $CO_2H$ |
| 33 | Cl | $CF_3$ | H | O | Me | H | 1 | $CO_2Na$ |
| 34 | Cl | $CF_3$ | H | O | Me | H | 1 | $CO_2K$ |
| 35 | Cl | $CF_3$ | H | O | Me | H | 2 | $CO_2Et$ |
| 36 | Cl | $CF_3$ | H | O | H | H | 4 | $CO_2Et$ |

What is claimed is:

1. A process for preparing a compound of the formula wherein X is hydrogen, halo, trihalomethyl, alkyl, cyano or nitro; $X^1$ is hydrogen, halo or trihalomethyl, $X^2$ is trihalomethyl or halo; $R^1$ and $R^2$ are the same or different radicals selected from hydrogen, lower alkyl or mononuclear aryl lower alkyl; n is an integer of from 1 to 5; and Z is carboxy, amino, monoalkylamino, or dialkylamino and when Z is carboxy, the agronomically acceptable salts, esters and amides thereof, which comprises treating a compound of the formula:

wherein X, $X^1$ and $X^2$ are as defined above and M is a cation derived from al alkali metal or alkaline earth metal base, with a compound of the formula; Halo($CR^1$-$R^2$)$_n$Z, wherein $R^1$, $R^2$, n and Z are as defined above and halo is chloro, bromo or fluoro in the presence of an inert solvent at a temperature in the range of from about 20° to about 150° C. followed by nitration at a temperature in the range of from about 20° to about 200° C.

2. A process for preparing a diphenyl ether of the graphic formula:

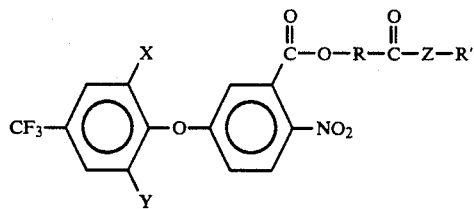

wherein X is hydrogen or halogen; Y is hydrogen, halogen, cyano, trifluoromethyl, or an alkyl radical containing from 1 to 4 carbon atoms; Z is oxygen or sulfur; R is a methylidene or monosubstituted methylidene, whrein the substituent is selected from the group consisting of alkyl, oxoalkyl and hydroxyalkyl radicals containing from 1 to 4 carbon atoms; and $R^1$ is hydrogen, or an alkyl radical containing from 1 to 8 carbon atoms, a cycloalkyl radical containing from 3 to 8 carbon atoms, an agronomically acceptable cationic salt, phenyl, or mono-,di-, or tri-substituted pehnyl, said substituents being selected from the group consisting of halogen, alkyl or alkoxy radicals containing from 1 to 10 carbon atoms, cyano, nitro, and trifluoromthyl; which comprises the sequential steps of:

(a) reacting a diphenyl ether of the graphic formula:

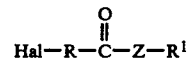

wherein X and Y are as defined above, with an inorganic alkali metal base to form the corresponding acid salt;

(b) reacting the acid salt of step (a) with an α-halocarboxylic acid ester of the graphic formula:

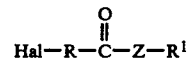

wherein R and Z are as defined above; $R^1$ is an alkyl radical containing from 1 to 8 carbon atoms, a cycloaklyl radical containing from 3 to 8 carbon atoms, phenyl, or mono-, di-,. or trisubstituted phenyl, said substituents being selected from the group consisting of halogen, alkyl or alkoxy radicals containing from 1 to 10 carbon atoms, cyano, nitro, and trifluormethyl; and Hal is selected from the group consisting of chlorine, bromine and iodine, to form the corresponding ester; and (c) nitrating the ester product of step (b) with a nitrating agent selected from the group consisting of nitric acid; mixtures of nitric acid and sulfuric acid; mixtures of potassium nitrate and sulfuric acid; and mixtures of nitric acid, sulfuric acid, and acetic anhydride, thereby to form a diphenyl ether represented by graphic Formula I.

3. The process of claim 2 wherein the inorganic alkali metal base is an alkali metal hydroxide.

4. The process of claim 2 wherein the nitrating agent is a mixture of nitric acid, sulfuric acid and acetic anhydride.

* * * * *

UNITED STATES PATENT AND TRADEMARK OFFICE
CERTIFICATE OF CORRECTION

PATENT NO. : 5,214,190

DATED : May 25, 1993

INVENTOR(S) : Wayne O. Johnson

It is certified that error appears in the above-identified patent and that said Letters Patent is hereby corrected as shown below:

Column 24:
Claim 1, lines 22-34, replace the formula with:

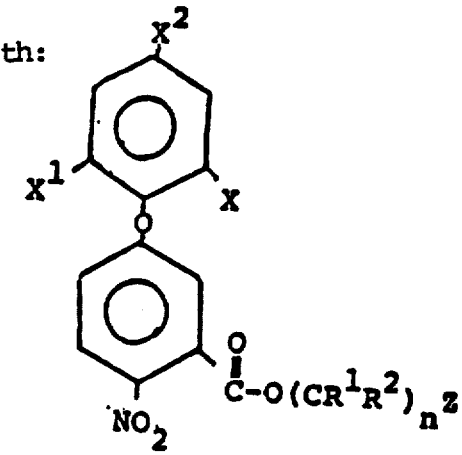

Claim 1, lines 45-58, replace the formula with:

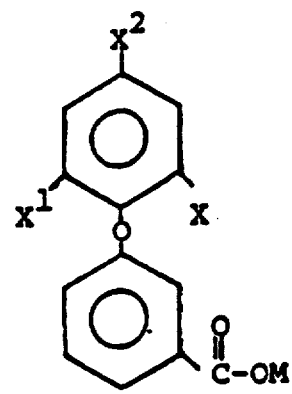

UNITED STATES PATENT AND TRADEMARK OFFICE
CERTIFICATE OF CORRECTION

PATENT NO. : 5,214,190
DATED : May 25, 1993
INVENTOR(S) : Wayne O. Johnson

It is certified that error appears in the above-indentified patent and that said Letters Patent is hereby corrected as shown below:

Column 24:
Claim 2, line 68, after "formula" and before ":", insert —I—.

Signed and Sealed this

Nineteenth Day of April, 1994

Attest:

BRUCE LEHMAN

Attesting Officer    Commissioner of Patents and Trademarks